United States Patent

Chechelski et al.

[19]

[11] Patent Number: 5,908,385
[45] Date of Patent: Jun. 1, 1999

[54] APPARATUS FOR MAPPING ELECTRICAL ACTIVITY IN A BODY AND TREATING TISSUE

[75] Inventors: Victor Chechelski, Mountain View; Jeffrey S. Frisble, San Jose; Paul D. Corl, Palo Alto; John E. Ortiz, E. Palo Alto, all of Calif.

[73] Assignee: Cardiometrics, Inc., Mountain View, Calif.

[21] Appl. No.: 08/599,223

[22] Filed: Feb. 8, 1996

Related U.S. Application Data

[63] Continuation-in-part of application No. 08/222,137, Apr. 1, 1994, Pat. No. 5,517,989.

[51] Int. Cl.$^6$ .......................... A61B 5/0408; A61B 8/06; A61N 1/05
[52] U.S. Cl. .......................... 600/374; 600/377; 600/381; 600/462; 600/505; 606/41; 607/122
[58] Field of Search .............................. 128/642, 661.08, 128/661.09, 662.06, 692, 702; 607/116, 119, 122; 606/41; 600/373, 374, 377, 378, 381, 462, 465, 467, 468, 505, 585

[56] References Cited

U.S. PATENT DOCUMENTS 5,509,411  4/1996  Littmann et al. ...................... 128/642
5,517,989  5/1996  Frisbie et al. ......................... 128/642

*Primary Examiner*—Lee S. Cohen
*Attorney, Agent, or Firm*—Flehr Hohbach Test Albritton & Herbert LLP

[57] ABSTRACT

A guide wire assembly comprises a tubular body having a distal end and an proximal end. At least a portion of the body comprises a single continuous helical spring to which one or more tubular electrodes are secured. The electrodes are insulated from the spring by means of an insulator. The electrodes can take a variety of forms, including conductive ribbons, longitudinally split conductive tubes, tubular sections, etc. The guide wire assembly may further include a variety of sensors, such as velocity sensors or temperature sensors. In order to allow flowable material to be passed to the distal end of the guide wire, the guide wire can include a catheter tube passable over the tubular body of the guide wire.

27 Claims, 5 Drawing Sheets

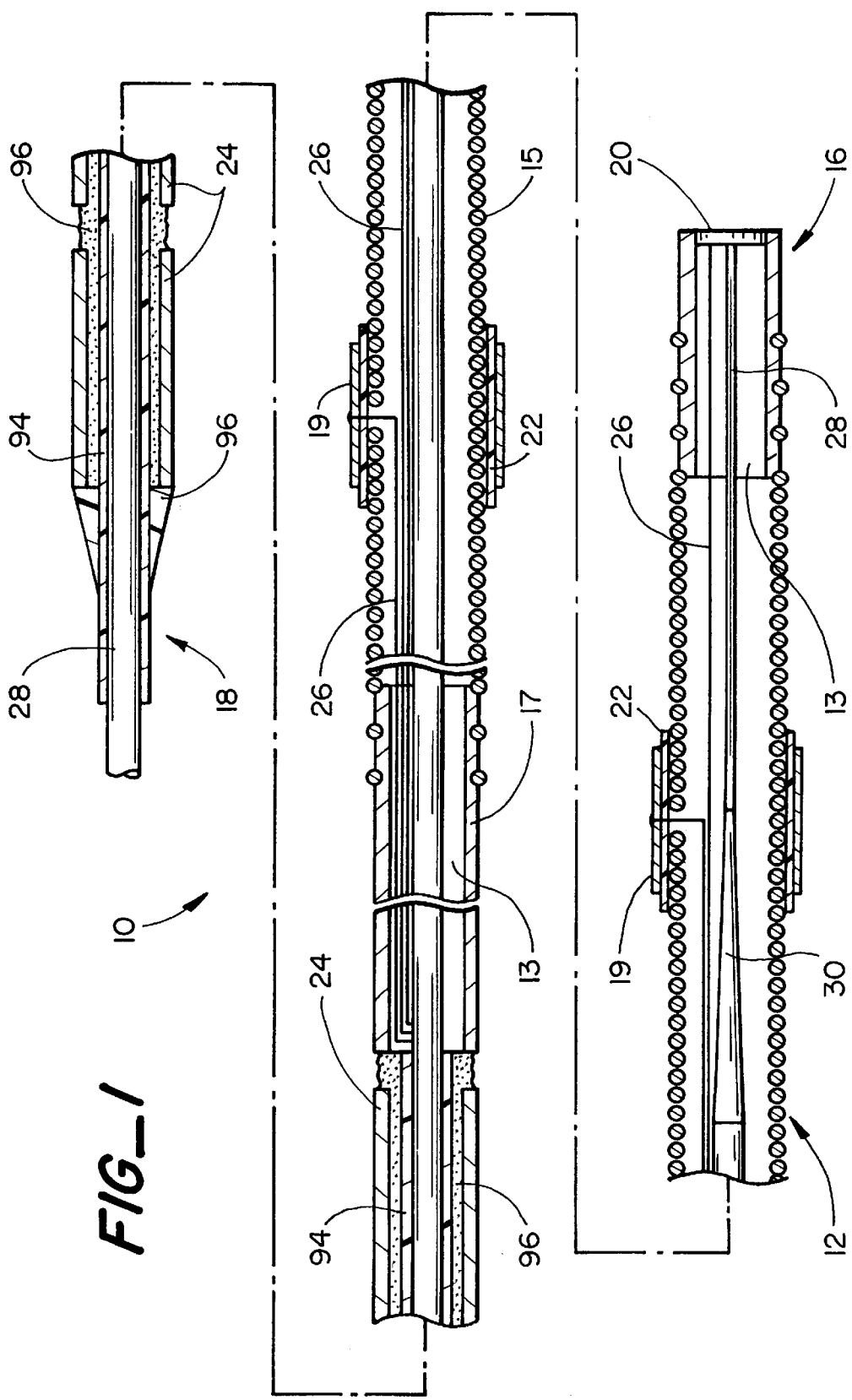

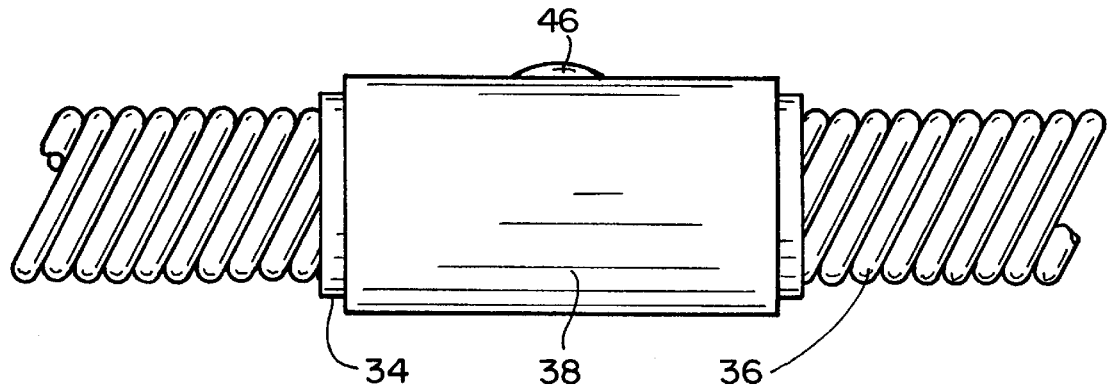
FIG_2
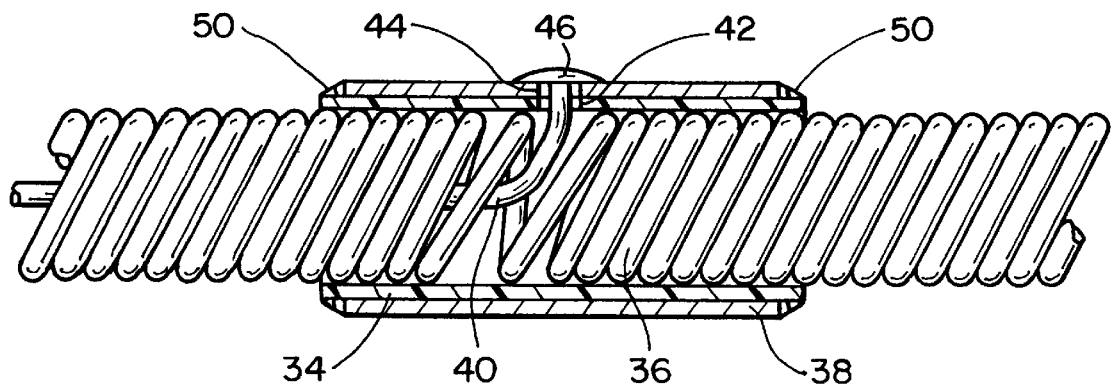
FIG_3
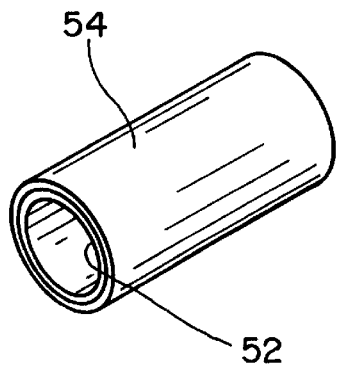
FIG_4

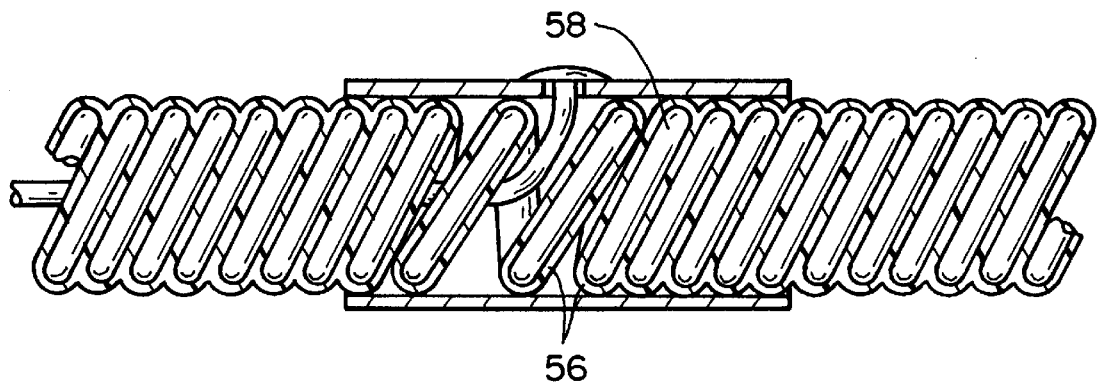
FIG_5
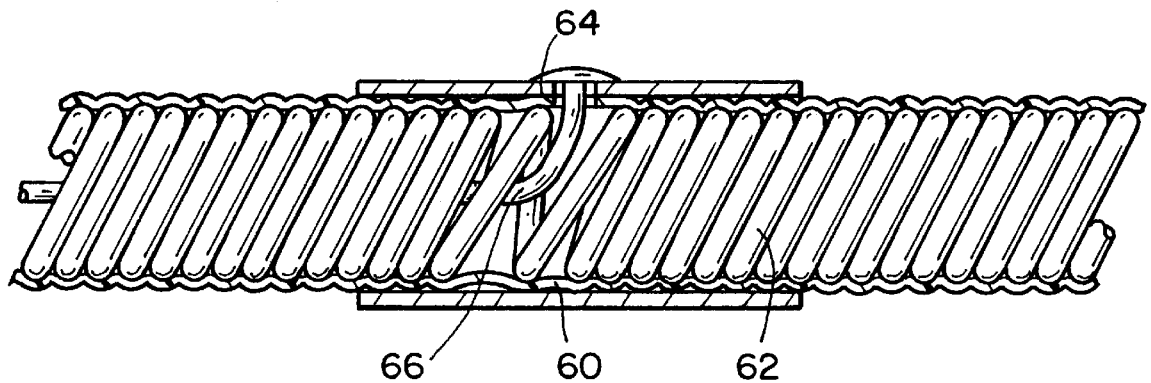
FIG_6
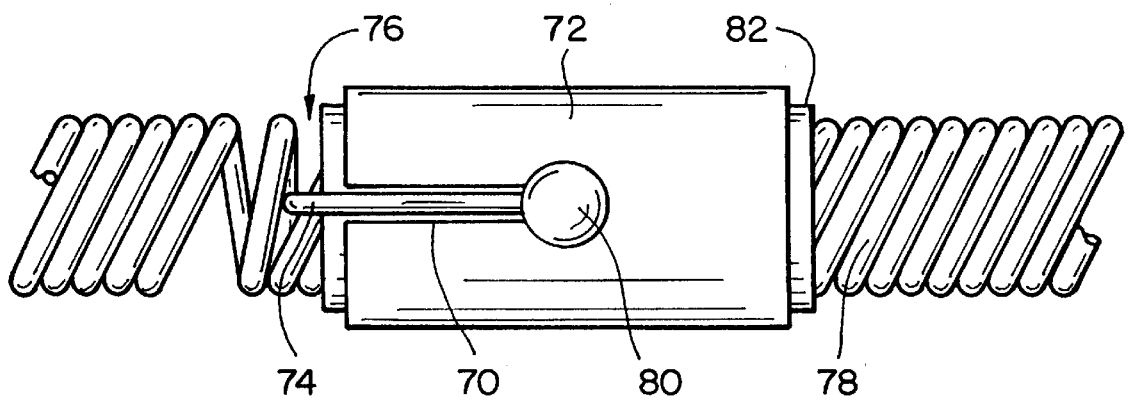
FIG_7

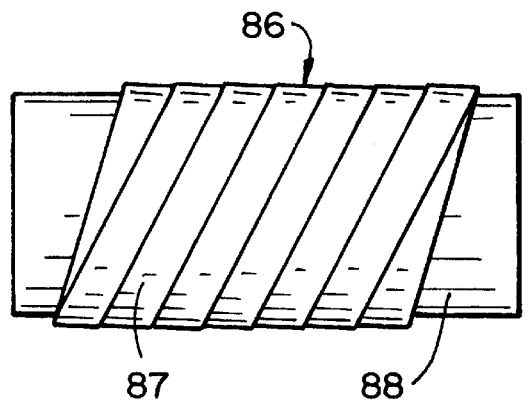
FIG_8
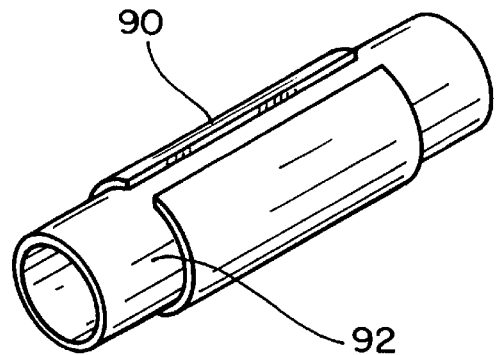
FIG_9
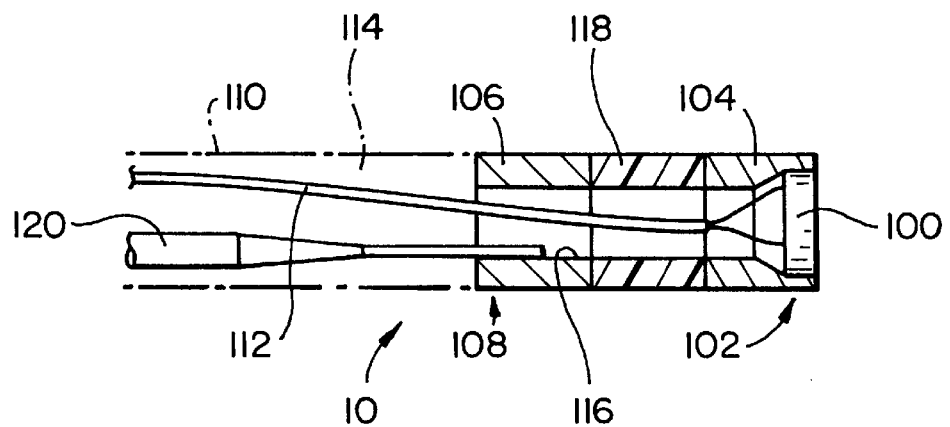
FIG_10

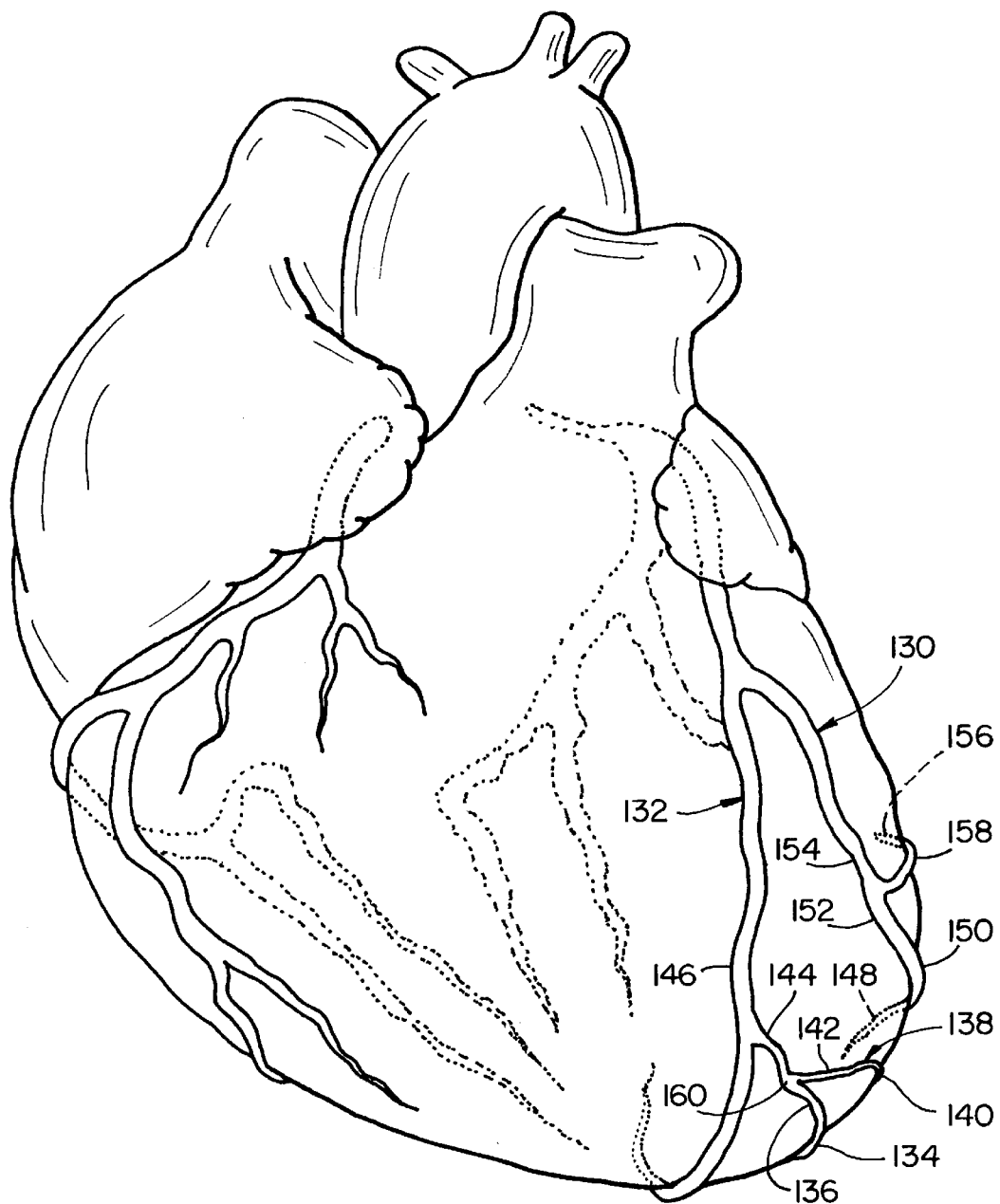
FIG_11

APPARATUS FOR MAPPING ELECTRICAL ACTIVITY IN A BODY AND TREATING TISSUE

RELATIONSHIP TO COPENDING APPLICATIONS

This patent application is a continuation-in-part of U.S. patent application Ser. No. 08/222,137 filed on Apr. 4, 1994, now U.S. Pat. No. 5,517,989, the entire contents of which are hereby incorporated by reference.

FIELD OF THE INVENTION

This invention relates to a method and an apparatus for diagnosis of medical conditions of the human or animal body. In particular it relates to a method and an apparatus for mapping electrical activity in, for example, the heart or brain to locate arrhythmias for subsequent treatment by means of ablation. It relates specifically to an epicardial approach to achieve this purpose.

BACKGROUND OF THE INVENTION

An abnormal condition of the heart's electrical conduction system can exist that causes irregular heartbeats. There are various forms of these abnormalities that can cause the irregular heartbeats, or arrhythmias, including coronary artery disease, cardiomyopathy, congenital and valvular heart disease, metabolic disorders, and drug toxicity. Arrhythmias are even known to develop in structurally normal hearts. Whichever the cause and manifestation of the arrhythmia, the irregular heartbeat results in disruption of the smooth contraction sequence of the heart muscle and compromises the heart's ability to pump blood out to the rest of the body.

It is thus important that a process should exist allowing the source of such arrhythmias to be located. Electrocardiographic mapping allows this to be achieved. In the past, electrocardiographic mapping, however, typically required open heart surgery in which a grid of electrodes was wrapped around the heart on the epicardial surface. In order to avoid open heart surgery and to allow the mapping to be performed percutaneously, endocardial mapping processes have been developed. These involve the insertion of a catheter into the heart chambers in order to probe the endocardial surfaces to locate the general area from which an arrhythmia emanates. Should intervention be desired in order to stop the arrhythmia, the precise location of its source must be known. While an endocardial approach allows the general location of the source of an arrhythmia to be determined, the epicardial approach will provide more accurate results. In particular it is desirable to be able to map the electrocardiographic patterns using a percutaneous technique. The present invention accordingly provides a means to achieve this by mapping the coronary arteries lying on the epicardial surface of the heart.

OBJECTS AND SUMMARY OF THE INVENTION

It is an object of the invention to provide an apparatus for mapping the electrical activity of the heart/brain.

It is a further object of the invention to treat heart disease by means of a guide wire.

Yet another object of the invention is to monitor the flow velocity of blood without invasive surgery and to combine this with a blood or tissue mapping or coagulation device inserted through the skin, also referred to as percutaneous treatment.

A further object of the invention is to provide a percutaneous tissue or blood coagulation device with a temperature sensing capability.

According to the invention there is provided a guide wire assembly comprising a tubular body having a distal end and a proximal end, and at least one electrode secured to an electrode supporting portion of the tubular body, wherein at least the electrode supporting portion of the tubular body comprises a single continuous helical spring.

The guide wire assembly can have lateral dimensions of from 0.010" to 0.038".

The at least one electrode can be secured to the body is a unipolar electrode. The body can include a smooth proximal sleeve section.

The guide wire assembly can further comprise an electrical conductor for each electrode, wherein each electrical conductor extends along a lumen defined by the tubular body.

The guide wire assembly could also comprise a centrally extending core extending at least along the full length of the tubular body. The core could constitute one of the electrical conductors.

The at least one electrode can be electrically insulated from the helical spring by means of an insulator. At least one of the at least one electrode can be a tubular electrode and can be insulated from the helical spring by means of an insulator in the form of an insulating layer between the helical spring and said at least one tubular electrode.

The insulating layer can comprise an insulating sleeve covering at least any portion of the helical spring corresponding to the at least one tubular electrode. The insulating layer can also comprise an insulating sleeve covering the helical spring and an insulating coating on at least any portion of the helical spring corresponding to the at least one tubular electrode. The insulating layer can further comprise an insulating coating on the helical spring, or an insulating layer formed on an inner surface of the at least one tubular electrode.

Each tubular electrode can comprise a conductive tube which is split longitudinally. Instead, the insulator can comprise a non-conductive tubular support, and the electrode can comprise a conductive ribbon wound on the tubular support. In another embodiment, each tubular electrode can comprise a conductive tube, adhesively secured to the helical spring by means of an adhesive, the adhesive forming the insulator between the electrode and the helical spring. Each tubular electrode can further comprise a conductive tube secured to an insulator that is, in turn, secured to the helical spring.

The guide wire assembly can include a velocity sensing means, such as a Doppler ultrasound transducer, connected to the body for sensing the velocity of blood flow in a blood vessel.

The guide wire assembly can further include a temperature sensor connected to the tubular body.

The guide wire assembly can also include a catheter tube means passable over the tubular body to define a pathway for passing flowable material along the pathway.

The lateral dimensions of the core can be such as to decrease towards the distal end of the body, and the decrease in the lateral dimensions of the core can comprise a plurality of discrete steps or a continuous gradual taper. The distal end of the core can be is flattened from a point between 1 cm and 1.5 cm from the distal end.

A distal portion of the body can be covered with a radio-paque material, and at least a distal portion of the helical spring can be stretched towards the distal end of the body to provide greater flexibility towards the distal end of the body.

Portions of the helical spring are typically stretched to permit the at least one electrical conductor to pass from within the tubular body to its electrode.

BRIEF DESCRIPTION OF THE DRAWINGS

FIG. 1 is a sectional side view of one embodiment of a guide wire in accordance with the invention;

FIG. 2 is a side view of part of another embodiment of a guide wire in accordance with the invention;

FIG. 3 is a partially cut-away side view of the part of the guide wire of FIG. 2;

FIG. 4 is a isometric view of one embodiment of an electrode for use with a guide wire of the invention;

FIG. 5 is a partially cut-away side view of part of yet another embodiment of a guide wire of the invention.

FIG. 6 is a partially cut-away side view of part of yet another embodiment of a guide wire in accordance with the invention;

FIG. 7 is a plan view of yet another embodiment of a guide wire of the invention.

FIG. 8 is a side view of one embodiment of an electrode and insulator in accordance with the invention;

FIG. 9 is an isometric view of another embodiment of an electrode assembly in accordance with the invention;

FIG. 10 is a sectional side view of another embodiment of the guide wire in accordance with the invention, showing the distal portion thereof, and FIG. 11 is a three-dimensional view of a human heart.

DETAILED DESCRIPTION OF THE INVENTION

An electrocardiographic mapping device is described in U.S. Pat. No. 5,156,151 and in U.S patent application Ser. No. 08/222,137, the entire contents of which are incorporated herein, by reference.

Referring to FIG. 1, a guide wire in accordance with one embodiment of the invention is indicated generally by reference numeral 10, and includes an elongate tubular body 12 defining a central elongate lumen 13. The body 12 is made of an electrically conductive material which comprises a spring coil 15 towards the distal end 16 of the body 12, and a smooth sleeve section 17 towards the proximal end 18. The body 12 can equally well be constructed from an electrically non-conductive material. The proximal end 18 is connected to a rotary connector (not shown). Two spaced apart, sleeve-like electrodes 19 surround the body 12 near its distal end 16 and an end electrode 20 is located on the distal end 16. The electrodes 19 are insulated from the spring 15 by insulating sleeves 22, and the electrodes 19, 20 are connected electrically to electrical contacts 24 by means of electrical conductors 26 extending longitudinally along the lumen 13 to the electrical contacts 24 mounted at the proximal end 18 of the tubular body 12.

In this embodiment, a core 28 extends along the length of the body 12 and provides the guide wire 10 with structural integrity and a certain amount of rigidity. The core 28 is tapered towards the distal end 16 to give the wire 10 greater flexibility towards the distal end 16. In the embodiment illustrated in FIG. 1, the tapering takes place in successive gradual steps, one of which is illustrated in FIG. 1 in the portion depicted by reference numeral 30. In this particular embodiment the tapering steps commence at locations approximately 15 to 20 centimeters from the distal end 16 (not shown), and 2 to 3 centimeters from the distal end 16 (depicted by numeral 30), respectively. Furthermore the core 28 is flattened from a point about 1 to 1.5 centimeters from the distal end 16 to define an oval cross section. The spring coil 15 is also stretched somewhat at its distal end (not shown) to provide the wire 10 with greater flexibility at the distal end 16.

As mentioned above, in this embodiment, each electrode 19 is electrically insulated from the spring coil 15 by means of a non-conductive support sleeve 22. The sleeve 22 is adhesively secured to the electrode 19, for example by means of an epoxy or a cyanoacrylate adhesive (not shown). The electrode portion is illustrated in greater detail in another embodiment of the guide wire assembly shown in FIGS. 2 and 3. In FIGS. 2 and 3 the sleeve 34 is secured to the spring coil 36 using any suitable means such as adhesive or a heat shrinking process. As discussed in greater detail below, the electrodes can be produced in a variety of ways including wrapping a conductive ribbon around a non-conductive support sleeve. Instead it can comprise a conductive layer spattered onto a non-conductive sleeve. Yet another option is to provide a conductive tube having a longitudinal split to provide a tubular electrode with a sufficient diameter to allow it to be slipped over an insulator, such as the sleeve 34 and then secured in place by a crimping process or using an adhesive. Yet another possibility is to provide a conductive cylinder having a diameter sufficient to be slipped over an insulator such as the sleeve 34 and secured to the sleeve, for example, using an adhesive. In the partially sectioned view illustrated in FIG. 3, the electrode 38 is shown to be connected to a conductor 40 that passes along the lumen defined by the spring coil 15 to the electrode 19 via a hole 42 formed in the sleeve 34 and a hole 44 in the electrode 38. The conductor 40 is anchored by means of solder 46. As is illustrated in FIG. 3, the spring 15 is slightly stretched in the region of the electrode 34 to permit the conductor 40 to pass through to the electrode 34. As is illustrated in FIG. 3, this embodiment of the guide wire, in accordance with the invention, dispenses with the core 28 illustrated in the FIG. 1 embodiment.

Since the electrode and its insulator extend radially from the surface of the coil spring 36, it is preferable to provide a tapered edge to the electrode 34, for example, by using a polymeric material 50 to create a beveled edge to the electrode structure illustrated in FIG. 3. For clarity of illustration the material 50 has not been illustrated in FIG. 2.

In another embodiment the electrodes can be insulated from the coil spring by means of an insulating layer 52 formed on the inner surface of the cylindrical electrode 54 as illustrated in FIG. 4.

In yet another embodiment of the invention the electrode can be insulated from the coil spring by means of an insulating coating 56 formed on the outer surface of the coil spring 58 as illustrated in FIG. 5. This coating can be formed in only the region occupied by the electrodes or can extend along a greater portion or all of the outer surface of the coil spring. In FIG. 5 the insulating coating 56 is indicated as covering the individual coils of the coil spring 58. It will be appreciated that the insulating coating could equally well constitute a sleeve-like structure 60 formed on the coils 62 and having a hole 64 for accommodating the conductor 66.

FIG. 7 is a plan view of part of yet another embodiment of a guide wire in accordance with the invention. In the embodiment illustrated in FIGS. 2 and 3, holes 42 and 44 were formed in the sleeve 34 and electrode 38. Instead, a slot 70 can be formed in the electrode 72 as illustrated in FIG. 7. The conductor 74 then extends through the spaced apart portion 76 of the coil 78 to the center of the electrode 72 via the slot 70. The conductor 74 is secured to the electrode by means of solder 80. It will be appreciated that instead of providing a slot 70, an embodiment could simply have the conductor secured to an edge of the electrode. In the embodiment illustrated in FIG. 7, the electrode 72 is, once again, mounted on an insulating layer 82.

Two embodiments of the electrodes formed on an insulating sleeve are depicted in FIGS. 8 to 9.

FIG. 8 shows the electrode 86 in the form of a ribbon 87, wrapped around an insulating tubular support 88.

In FIG. 9, the electrode comprises a split cylinder 90 crimped onto an insulating sleeve 92. (end of tape)

Referring again to FIG. 1, the spring coil 15 making up the distal part of the body 12 is typically coated at its distal end with a radiopaque material, e.g. any of various alloys of platinum, palladium or gold, to make the distal end more easily visible under X-rays. The core 28 is made of stainless steel or nickel titanium.

The contacts 24 are electrically insulated from the core 28 by means of a sheath 94 of a thin-walled material such as polyamide intermediate the contact 24 and the core 28. The contacts 24 are secured to the sheath 94 by means of an adhesive 96, for example an epoxy, a moisture cure or a light cure (typically ultra violet light). The adhesive 96 also serves to smoothen the transition between the contacts 24 and the body 12. The electrical conductors 26 are secured to the contacts 24 and electrodes 19, 20 by means of a soldering process.

Instead of merely serving as a means for mapping and ablating by virtue of the electrodes, the wire 10 may further include sensors for measuring blood flow velocity in the blood vessel and/or the temperature of blood or tissue. Referring, for instance, to FIG. 10, a guide wire 10 having a sensor 100 attached to its distal end 102, is illustrated. The sensor 100 may be a Doppler ultrasound transducer for measuring the blood flow velocity in a blood vessel or may be any other desired sensor, e.g. for measuring the temperature of tissue. In the illustrated embodiment the sensor 100 is mounted on its own housing 104.

An electrode 106 is secured to the distal end 108 of the spring coil 110 between the coil 110 and the sensor housing 104. Conductors 112, connecting the sensor 100 to associated circuitry located externally to the wire 10, extend into the lumen 114 and pass through a central opening 116 in the electrode 106. The sensor 100 is thus connected electrically to electrical circuitry (not shown), at the proximal end of the body by means of the electrical conductors 112. If the housing 104 is made from an electrically conductive material, the housing 104 is electrically insulated from the electrode 106 by means of a cylindrical insulator 118 intermediate the electrode 106 and the housing 104. In this embodiment, the core 120 serves as a conductor connecting the electrode 106 with a contact (not shown). In order electrically to insulate the core 120 from the conductors 112, the core 120 is provided with an insulating coating (not shown). It will be appreciated that, instead of using the core 120 as a conductor, the electrode 106 could be connected to its contact by means of a separate conductor similar to the conductors 112.

The guide wire 10 has numerous applications. It can, for instance, be used to map electrical activity from any suitable blood vessel e.g. in the heart or the brain. For convenience, the description below refers specifically to the use of the wire 10 in coronary arteries.

The guide wire 10 may be manipulated along a suitable blood vessel into a desired coronary artery to perform functions epicardially. The electrodes allow epicardial mapping to be performed by monitoring the electrocardial patterns, as is described in greater detail below. Thereby arrhythmias can be located. In addition, a sensor attached to the guide wire 10 may be used to measure blood flow velocity, temperature or any other variable of interest depending on the nature of the sensor. The electrodes perform the further function of ablation by connecting a direct current or radio frequency voltage source to the electrical contacts 24. One or more suitable electrodes may be placed externally to the electrodes on the wire 10 for selective coagulation of body tissue. Instead, a potential difference may be established across any two electrodes on the wire 10 to cause ablation of tissue intermediate these two electrodes.

If a patient presents with an irregular heartbeat, the region from which it originates can be determined generally using electrocardiograms. However, if intervention is desired in order to stop the arrhythmia, the precise location must be known. As mentioned above, current methods for determining the location include percutaneously inserting an electrode catheter into one of the heart chambers and positioning it at various locations on the chamber's endocardial surface to locate the general location of an arrhythmia. Another, more accurate, method requires open heart surgery in which the chest is opened and the heart exposed. Electrodes are then placed at various points on the epicardial surface. With the present invention, a very precise epicardial approach can be accomplished percutaneously, rather than opening the chest, by inserting the guide wire 10 of the present invention into the coronary arteries, which lie on the epicardial surface of the heart.

Referring to FIG. 11, the guide wire 10 is used to generate an electrical map of the arterial system of the heart to precisely locate the origin of an arrhythmia, the approximate location of which may have been previously determined through the use of electrodes on the body surface. The guide wire 10 is steered into any of the coronary arteries or their branches. Access to the arteries is percutaneous using standard techniques either from the femoral or brachial artery. Each unipolar electrode on the wire is capable of sensing the local electrical activity of the heart muscle. The activity at various points along the length of an artery, and possibly in several arteries, is sampled as discussed in greater detail below. The origin of the arrhythmia is then localized by comparing the sampled signals and determining the earliest occurrence. Any stationary electrode, such as a surface electrode, is used as a reference signal. With multiple electrodes on the wire, multiple sites can be sampled simultaneously. The device thus needs to be repositioned fewer times, and the mapping procedure may be accomplished more quickly.

In practice intravascular mapping would involve first locating the general site of the arrhythmia. In this case the electrocardiographic assessment reveals the arrhythmia to be in the tissue served by the left anterior first diagonal artery 130 and left anterior descending artery 132. Now the specific branch needs to be determined. For the purposes of this example, a guide-wire 10 having two unipolar electrodes 19 is used.

The wire 10 is initially positioned with its distal end 16 in the distal region of the second diagonal. The two electrodes 19 are positioned such that they sample the activity at points 134 and 136. An arrhythmia is then induced by applying electrical pulses using an endocardial pacing lead. While the arrhythmia is sustained measurements are made. The wire 10 is then repositioned into the branch 138 of the second diagonal so that the two electrodes 19 are positioned at points 140 and 142, and the procedure is repeated. This is similarly done for points 144 and 146. The wire is then repositioned into the first diagonal branch 130 and the sequence of measurements repeated for points 148 and 150, 152 and 154, and 156 and 158. By comparing the timings of the electrical impulses from all the measurements with reference to a surface electrode, the location of the arrhythmia can be determined by selecting the sample point with the earliest occurrence.

A general premise for the search procedure is to locate the earliest occurring signal. A modification to the mapping procedure just described could be to interrogate the arteries, always repositioning the device toward the earlier occurring signal. With a two-electrode device as described, the signals from the two electrodes 19 are compared and if the signal from the proximal electrode is earlier, the wire 10 is retracted for the next reading; if the distal signal is earlier, the wire 10 is advanced.

Assuming the location of the arrhythmia is determined to be in the region of sample points 140 and 142, this can be confirmed by injecting a dose of iced saline into the vessel at that location. A small catheter is slid down over the guide wire 10 such that the distal tip of the catheter is beyond the bifurcation 160 and just proximal to sample point 142. While monitoring the activity distal to the catheter, and while the arrhythmia is present, cold saline is injected. The cold saline will temporarily stun the heart tissue locally and if that tissue is the site of the arrhythmia, the arrhythmia will cease. Embolization can then proceed.

Embolization (i.e., clogging) of the target artery will cause infarction of the ischemic tissue, thus permanently eliminating the arrhythmia. For the present example, the wire 10 is positioned in the branch 138 of the second diagonal so that the distal electrode is approximately at sample point 142. The electrode is then energized with sufficient RF energy to cause heating and coagulation of the blood at and near the electrode site. The coagulation will embolize the artery distal to the electrode. Embolization can be confirmed by injecting a small amount of contrast medium.

Just as the heart has its electrical activity which can be demonstrated on electrocardiograms, the brain also has its own electrical activity which can be demonstrated on electroencephalograms. It will thus be appreciated that the device of the present invention can be used in the cerebral vasculature to map the brain's electrical activity, just as it can in the coronary arteries to map the heart's activity.

It will also be appreciated by those skilled in the art that the size and steerability of the wire 10 make it ideally suited for the purpose of insertion into even very small veins and arteries.

As mentioned above, the wire 10 may be used in conjunction with a catheter tube which is slid over the wire 10 once the appropriate site has been located. Apart from saline, other flowable material may also be fed down the tube to cause, for example cell destruction. Similarly the tube may serve to drain flowable material from the site. In this context, the term flowable material includes not only fluids but also small solid particles dimensioned to pass along the tube e.g. tissue particles which have been removed from the parent tissue, or particles of degenerated material intima.

It will further be appreciated that the wire 10 may equally well be used in conjunction with a dilatation balloon or other interventional catheter to treat appropriate problem areas in the same setting as for the mapping and/or ablation procedures.

The invention claimed is:

1. A guide wire assembly comprising a tubular body having a single continuous helical spring forming at least a portion thereof, an insulative sleeve covering at least a portion of the helical spring, and a tubular electrode mounted on the body over the insulative sleeve with the sleeve insulating the electrode from the spring.

2. The guide wire assembly of claim 1 wherein the assembly has lateral dimensions of from 0.010" to 0.038".

3. The guide wire assembly of claim 1 wherein the electrode is a unipolar electrode.

4. The guide wire assembly of claim 1 wherein the body includes a smooth proximal portion.

5. The guide wire assembly of claim 1 further comprising an electrical conductor connected to the electrode and extending along a lumen within the tubular body.

6. The guide wire assembly of claim 1 further comprising a central core extending along the full length of the tubular body.

7. The guide wire assembly of claim 6 wherein the core comprises an electrical conductor which is connected to the electrode.

8. The guide wire assembly of claim 6 wherein the core decreases in lateral dimension toward a distal end of the tubular body.

9. The guide wire assembly of claim 8 wherein the core decreases in the lateral dimension in a plurality of discrete steps.

10. The guide wire assembly of claim 8 wherein the core decreases in the lateral dimension in a continuous gradual taper.

11. The guide wire assembly of claim 8 wherein a distal end portion of the core is flattened from a point between 1 cm and 1.5 cm from a distal end of the core.

12. The guide wire assembly of claim 1 wherein the insulative sleeve covers the entire helical spring.

13. The guide wire assembly of claim 1 wherein the tubular electrode is secured to the insulative sleeve, and the insulative sleeve is secured to the helical spring.

14. The guide wire assembly of claim 1 further including means connected to the body for sensing the velocity of blood flow in a blood vessel.

15. The guide wire assembly of claim 14 wherein the means for sensing the velocity of blood flow includes a Doppler ultrasound transducer.

16. The guide wire assembly of claim 1 further including a temperature sensor connected to the tubular body.

17. The guide wire assembly of claim 1 further including a catheter tube passable over the tubular body to define a pathway for flowable material.

18. The guide wire assembly of claim 1 wherein a distal portion of the body is covered with a radiopaque material.

19. The guide wire assembly of claim 1 wherein a distal portion of the helical spring is stretched to provide greater flexibility toward a distal end of the body.

20. The guide wire assembly of claim 1 wherein a portion of the helical spring is stretched to permit an electrical conductor to pass from within the tubular body to the electrode.

21. The guide wire assembly of claim 20 wherein the electrode has a longitudinally extending slot formed in one side thereof, and the conductor passes through the body adjacent to one end of the electrode, extends within the slot and is connected to the electrode midway between the ends of the electrode.

22. The guide wire assembly of claim 20 wherein the conductor passes through the body adjacent to one end of the electrode and is connected to the electrode at the one end.

23. The guide wire assembly of claim 1 wherein the insulative sleeve comprises a coating on the helical spring.

24. The guide wire assembly of claim 1 wherein the insulative sleeve comprises an insulative layer on an inner surface of the tubular electrode.

25. The guide wire assembly of claim 1 wherein the electrode comprises a conductive tube which is split longitudinally.

26. The guide wire assembly of claim 1 wherein the electrode comprises a conductive ribbon wound on the insulative sleeve.

27. The guide wire assembly of claim 1 wherein the insulative sleeve is formed by an adhesive which secures the tubular electrode to the helical spring.

* * * * *